United States Patent
AlGhamdi

(10) Patent No.: US 8,506,594 B2
(45) Date of Patent: Aug. 13, 2013

(54) GLIDING STITCH FOR CLOSING WOUNDS UNDER TENSION

(75) Inventor: Khalid M AlGhamdi, Riyadh (SA)

(73) Assignee: King Saud University, Riyadh (SA)

( * ) Notice: Subject to any disclaimer, the term of this patent is extended or adjusted under 35 U.S.C. 154(b) by 979 days.

(21) Appl. No.: 12/463,343

(22) Filed: May 8, 2009

(65) Prior Publication Data

US 2009/0281569 A1 Nov. 12, 2009

Related U.S. Application Data

(60) Provisional application No. 61/051,512, filed on May 8, 2009.

(51) Int. Cl.
*A61B 17/04* (2006.01)
(52) U.S. Cl.
USPC .......................................................... 606/228
(58) Field of Classification Search
USPC .................... 606/139, 144–148, 222–233
See application file for complete search history.

(56) References Cited

U.S. PATENT DOCUMENTS

| 4,696,301 | A | 9/1987 | Barabe |
| 5,127,412 | A | 7/1992 | Cosmetto et al. |
| 6,471,715 | B1 | 10/2002 | Weiss |
| 7,144,412 | B2 | 12/2006 | Wolf et al. |
| 7,875,043 | B1 * | 1/2011 | Ashby et al. .................. 606/148 |
| 2005/0096699 | A1 * | 5/2005 | Wixey et al. .................. 606/232 |

OTHER PUBLICATIONS

Stough DB, Spencer DM, Schander CS. New devices for scalp reduction; intraoperative and prolonged scalp extension. Dermatol Surg 1995; (21):777-80.
Distasio AJ, Dugdale TW, Deafenbaugh MK. Multiple relaxing skin incisions in Orthopeadic lower Extremity Trauma. J Orthop Trauma, 1993; 7(3):270-274.
Giandoni MB,Grabski WJ. Surgical pearl: The dermal buried pulley suture. J Am Acad Dermatol 1994; (30):1012-3.
Casparian JM, Monheit GD. Surgical pearl :The winch stitch a multiple pulley suture. J Am Acad Dermatol 2001; (44):114-6.
Liu CM, Mekenna J, Griess A. Surgical pearl: The use of towel clamps to reapproximate wound edges under tension. J Am Acad Dermatol 2004; (50):273-4.
Coldiron BM. Closure of wounds under tension: The horizontal mattress suture. Arch. Dermatol 1989; (125):1189-90.
Salaschee SJ, Whalen JD, Dufrescue RG, Collins SC. Surgical pearl: The modified buried dermal suture. J Am Acad Dermatol 1999; (40):103-4.

* cited by examiner

*Primary Examiner* — Thomas McEvoy
(74) *Attorney, Agent, or Firm* — Steven A. Nielsen; Allman & Nielsen, P.C.

(57) ABSTRACT

A gliding stitch technique provides efficient and effective means to close a wound under tension. The gliding stitch is especially useful in treating wounds found within thick skin such as a scalp or back wound. The disclosed suture method may be used upon humans and other mammals.

1 Claim, 3 Drawing Sheets

GLIDING STITCH FOR CLOSING WOUNDS UNDER TENSION

RELATED PATENT APPLICATION AND INCORPORATION BY REFERENCE

This is a utility application based upon U.S. patent application Ser. No. 61/051,512, entitled "Gliding Stitch for Closing Wounds Under Tension" filed on May 8, 2008. This related application is incorporated herein by reference and made a part of this application. If any conflict arises between the disclosure of the invention in this utility application and that in the related provisional application, the disclosure in this utility application shall govern. Moreover, the inventors incorporate herein by reference any and all patents, patent applications, and other documents hard copy or electronic, cited or referred to in this application.

BACKGROUND OF THE INVENTION (1) Field of the Invention

The invention generally relates to means and methods of closing wounds of humans and other mammals. More particularly, the invention relates to a technique of applying a suture to close a wound in tension, especially a wound in thick skin, such as scalp or back wound (2) Description of the Related Art Several techniques and devices that attempt to close skin wounds under tension are known in the art. For example, U.S. Pat. No. 6,471,715 Suture tightening device for closing wounds and methods for its use by Weiss, issued on Oct. 29, 2002 discloses a suture tightening wound closure device that includes the use of plates on either side of a wound and skin piercing stickers under the plates and other cumbersome, damaging and expensive mechanical parts. The device and technique of Weiss lead to an excessive amount of skin penetrations. The device used by Weiss to thread and/or install the plates is unduly complex and makes bandaging the wound difficult.

U.S. Pat. No. 5,127,412 Skin tensioning by Cosmetto et al, issued on Jul. 7, 1992 discloses a skin tensioning kit that resembles a mechanical pulley system with a bulky winder wheel assembly that stays attached to the wound victim. The winder of Cosmetto causes the suture or thread material to be tightened and secured at an elevation above the skin surface. The raised suture system of Cosmetto applies an upward ripping pressure on the skin where the sutures first penetrate the skin near each plate.

Other methods to assist in the closure of wounds under tension include: utilizing a layered closure, tissue expanders, an assistant or second pair of hands to push the wound edges together, Pulley stitch or Far-near-near-far suture, Winch stitch, towel clamps, horizontal mattress suture, and multiple relaxing skin incisions. These other methods and/or devices have numerous shortfalls and risks.

The use of tissue-expanding devices such as the sure-closure device and the Frechet extender is costly and may also place a mechanical load on or in the skin as the two sides of a wound are stretched together. An assistant's extra hands within the confines of a wound area may be awkward and a qualified assistant may not always be available. The far-near-near-far technique may result in unsightly scar tissue or cosmetic imperfections due to tension on the epidermis. A towel clamp is not suitable for areas of thin skin such as the face, as the towel clamp may cause the skin to tear. Multiple relaxing skin incisions cause trauma to the skin surrounding the wound area and a risk of scarring.

The horizontal mattress suture presents a risk of compromise to the blood supply to the wound area. Due to this risk factor, bolsters are sometimes used if the horizontal mattress suture is to be left in for additional support.

Despite advances of the related art, the primary repair of high-tension defects or skin wounds under tension is still difficult, risky, time consuming and expensive. Thus, there is a need in the art for additional means of wound closure.

BRIEF SUMMARY OF THE INVENTION

The present invention overcomes shortfalls in the related art by presenting an effective and efficient method of closing wounds under tension that eschews the use of assistants, cumbersome mechanical systems, skin piercing stickers, plates and the use of mechanical creep. The present invention may be implemented by a qualified medical professional with a standard surgical kit or standard first aid trauma kit. The disclosed technique uses previous methods in an unobvious combination to achieve unexpected results, especially when used in thick skin areas such as the scalp or back.

REFERENCE NUMBERS

Figure 1:
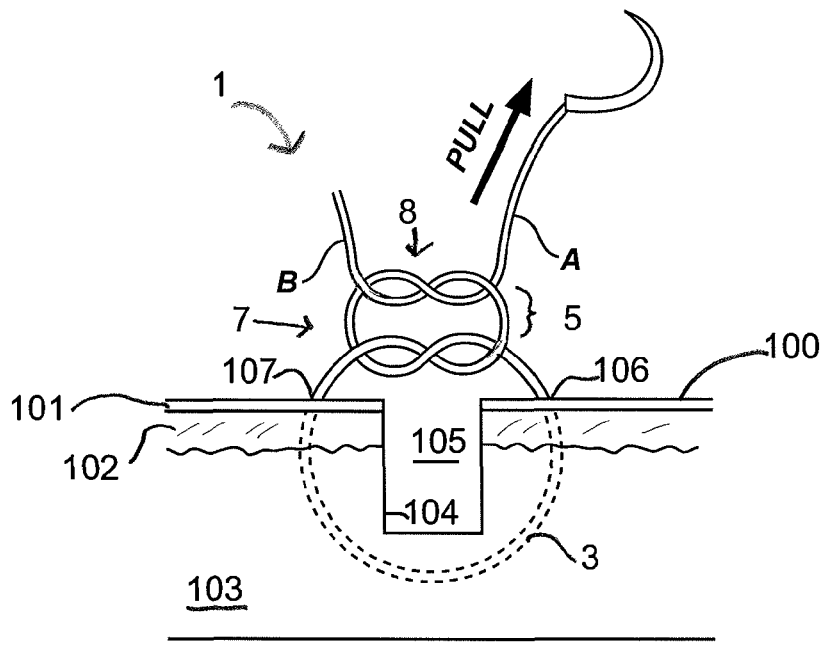
FIG. 1 is an elevation view of the disclosed method in a state wherein two loose loops are above the wound area.

A the thread end or thread side connected to the needle holder
B the thread end opposite to the A side of the thread
1 suture in loose loop position with two loose loops over the wound
2 suture configuration after A side is pulled upward and the lower loop 7 has glided over the B side of thread of the lower loop 7
3 surgical suture thread, preferably a monofilament suture such as prolene or nylon.
4 needle
5 instrument tie comprising a lower loop 7 and an upper loop 8
6 needle holder
7 lower loop of instrument tie 5
8 upper loop of instrument tie 5
100 outer surface of epidermis
101 layer of epidermis
102 layer of dermis
103 subcutaneous layer
104 surface of wounded skin tissue
105 wound void defined by surface of wounded tissue 104
106 first side of wound where needle is first inserted
107 second side of wound where needle emerges to the epidermis surface 100

DETAILED DESCRIPTION OF EMBODIMENTS OF THE INVENTION

The present invention is sometimes described here as the "Gliding Stitch", "gliding stitch", the "invention" and/or the "disclosed invention". The upward direction means at a direction away from the skin surface. The downward direction means the direction into the skin of the patient.

In the following description, for purposes of explanation, numerous specific details are set forth in order to provide a thorough understanding of the invention. It will be apparent, however, to one skilled in the art that the invention can be practiced without these specific details. In other instances, structures and devices are shown in block diagram form in order to avoid obscuring the invention.

The reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment nor are separate alternative embodiments mutually exclusive of other embodiments.

In the following detailed description of embodiments of the invention, reference is made to the accompanying drawings in which like references indicate similar elements, and in which is shown by way of illustration specific embodiments in which the invention may be practiced. These embodiments are described in sufficient detail to enable those skilled in the art to practice the invention, and it is to be understood that other embodiments may be utilized and that logical, mechanical, electrical, functional, and other changes may be made without departing from the scope of the present invention. The flowing detailed description is, therefore, not to be taken in a limiting sense.

The description, which follows, and the embodiments described therein, are provided by way of illustration of an example, or examples of particular embodiments of the principles of the present invention. These examples are provided for the purposes of explanation, and not of limitation, of those principles of the invention. In the description, which follows, like parts are marked throughout the specification and the drawings with the same respective reference numerals. The drawings are not necessarily to scale and in some instances proportions may have been exaggerated in order to more clearly depict certain features of the invention.

One embodiment of the Gliding Stitch may be described as follows:

Step 1

A needle 4 is attached to the needle holder 6 of a suture thread 3. The needle then penetrates a first side 106 of the wound, the epidermis 101, dermis 102, and upper subcutaneous tissue 103. The wound is crossed to the opposite side 107, looping a substantial portion of dermis and possibly subcutaneous tissue. As a result, the needle appears on the skin surface 100 of the opposite side 107 of the wound.

Step 2

An instrument tie 5 is preformed, with one throw only of the longer tail, shown as the needle side A, labeled "A" in FIG. 1, in either a clockwise or counterclockwise direction. The tip of the shorter tail is held by the needle holder and pulled within the loop. It should not be tied to the end, as a small loop should be left over the wound as shown in FIG. 1.

Step 3

The needle holder is used again to make one throw in the same direction as used in Step 2. The short tail is then grasped with the needle holder and pulled within the loop. It should not be tied to the end (i.e., a small loop should be left). By this stage, two loose loops will be seen as shown in FIG. 1.

Step 4

Figure 2:
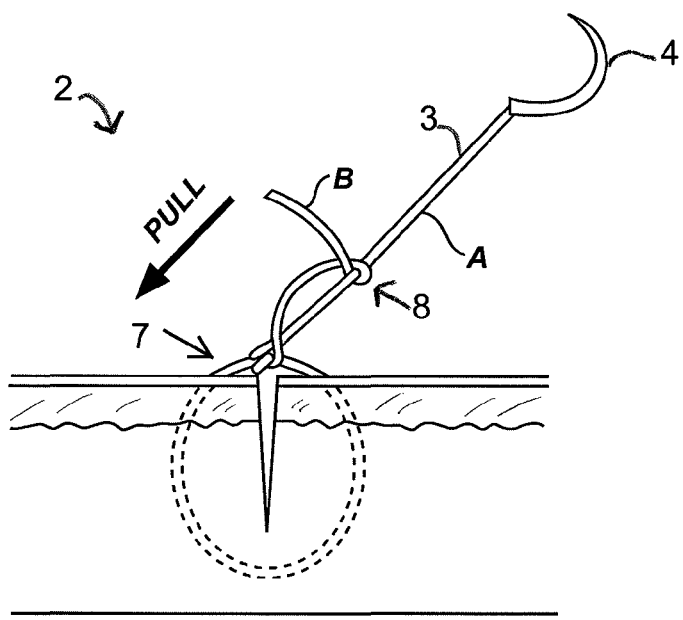
FIG. 2 is an elevation view of the longer "A" tail pulled upward.

The longer "A" tail on the needle side is pulled by the hand in an upward direction until the end. Thus, the lower loop will glide over the longer tail. As a result, the lower loop is completely tied as shown in FIG. 2.

Step 5

Figure 3:
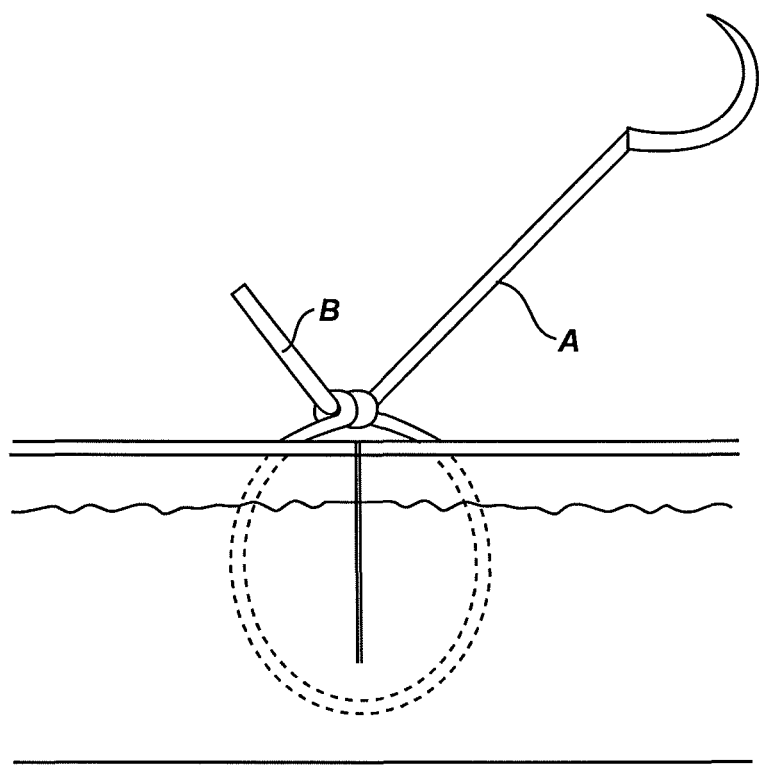
FIG. 3 is an elevation view of the shorter "B" tail pulled downward.

The shorter "B" tail, which is held by the needle holder, is pulled in a downward direction, causing the upper loop to glide over the longer "A" tail. As a result the remaining upper loop is tied as shown in FIG. 3. This completes the gliding stitch.

Further Details

To prevent unraveling, two additional throws in opposing directions are required. The present invention is sometimes called a "gliding" stitch because of the gliding of both of its loops over the needle attached tail.

Figure 4:
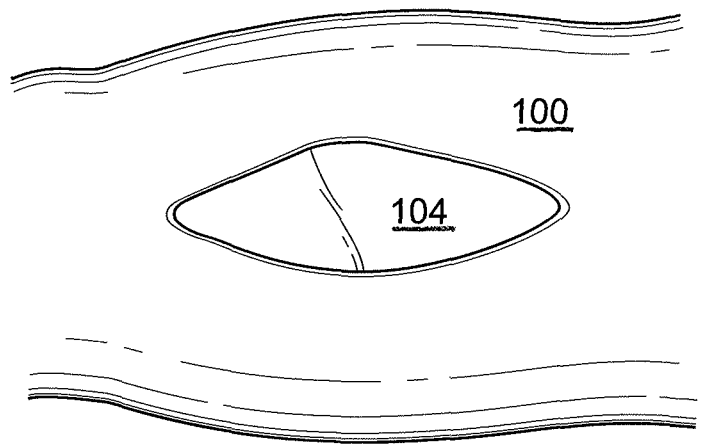
FIG. 4 is a perspective view of a sheep leg with a wound under tension and before the disclosed gliding stitch is applied.
Figure 5:
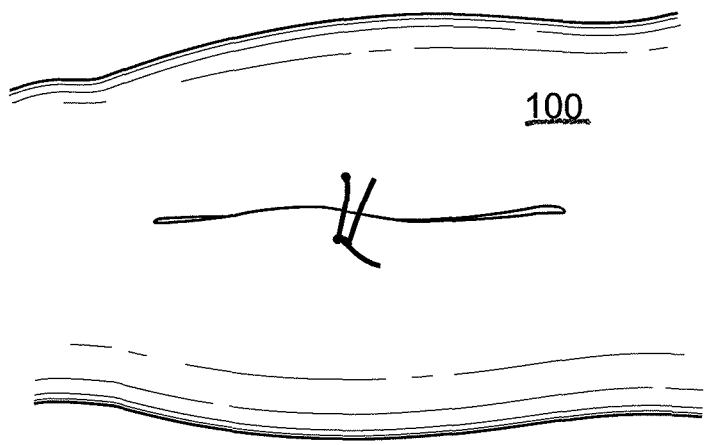
FIG. 5 is a perspective view of the wound of FIG. 4 after the application of the disclosed gliding stitch on and in the center of the wound.

The gliding stitch has some potential limitations and/or caveats. The gliding stitch may take longer amount of time to apply as compared to conventional suturing. Also, if left in postoperatively, the stitch may cause vascular compromise of the wound edges (FIGS. 4 and 5).

A monofilament suture like prolene or nylon should be used because of its smooth surface, which has a good potential for gliding. Also recommended is the use of a thick suture (e.g., at least 2-0 or 3-0) due to the fact that a finer suture will not tolerate tension. This stitch is a temporary one to bear tension and may be used in the middle of a wound. Subcutaneous sutures may then be easily applied. Subsequently, the gliding stitch may be removed and surface sutures will be applied.

A large skin or flesh wound may be comprised of a large void 105 defined by wound surface 104 which may penetrate various layers of skin. The closure of a large wound, such as the wound shown in FIG. 1 requires tension on either side of the wound to close the void 105 and to bring the wound surface 104 area to a closed state to facilitate healing of the wound area. The closure of such a wound is sometimes called "closing a wound under tension". The disclosed method achieves unexpected results by creating a loose instrument tie 5 comprising an upper loop 8 and a lower loop 7 and by closing or tightening each loop in a unique manner. The lower loop 7 is tightened first by pulling the A side of the thread in an upper direction, causing the sides of the wound to close together in a manner that does not require an extra set of hands to finish the procedure. A second set of hands are not needed, as the lower loop stays secure by one hand pulling upwardly on the A side while the other pulls the B side in a downward direction to complete the instrument tie.

These and other features make the gliding stitch an easy and effective technique which may be effectively and safely used to close wounds under tension.

Items

The invention includes, but is not limited to the following items:

[Item 1.] A surgical method of closing a wound within skin, the method comprising the steps of:
a) using a surgical suture thread 3 connected to a needle holder and needle to penetrate a first side 106 of a wound 105, with the needle and thread penetrating epidermis 101, dermis 102 and upper subcutaneous tissue 103;
b) looping the needle and thread 3 under the wound 105, looping a substantial portion of dermis and, if necessary, subcutaneous tissue;
c) directing the needle and thread 3 to a second side 107 of the wound;
d) manipulating the thread section A closest to the needle 4 to create a lower loop 7 of an instrument tie 5 with an opposite thread end B, wherein the instrument tie leaves a lower loop 7 over the wound 105 as the lower loop 7 is not tightened;

e) manipulating the thread section closest to the needle to create an upper loop 8 such that the upper loop is not tightened and loose thread rests between the upper loop 8 and the lower loop 7;
e) pulling by hand the needle side A of the thread in an upper direction causing the lower loop 7 to glide over the B side of the thread until the lower loop is tied to the wound, but leaving the upper loop 8 in a loose state;
f) pulling by hand the B side of the thread causing the upper loop 8 to glide over the A side thread, placing the upper loop 8 in a closed position adjacent to the wound and closed lower loop 7.

[Item 2] The method of item 1 wherein two or more additional throws in opposing directions are applied to reduce unraveling.

What is claimed is:

1. A surgical method of closing a wound, the method comprising the steps of:
   a) using a surgical suture thread having a first end connected to a needle holder and needle to penetrate a first side of a wound, with the needle and first thread end penetrating epidermis, dermis and upper subcutaneous tissue;
   b) looping the needle and first thread end under the wound looping a substantial portion of dermis and, if necessary to close the wound, subcutaneous tissue;
   c) directing the needle and first thread end to a second side of the wound;
   d) manipulating the first thread end to create a lower loop of an instrument tie with a second thread end, the second thread end being opposite to the first thread end and the second thread end located above the epidermis, wherein the instrument tie leaves a lower loop over the wound as the lower loop is not tightened;
   e) manipulating the first thread end to create an upper loop such that the upper loop is not tightened and loose thread rests between the upper loop and the lower loop;
   f) pulling by hand the first thread end in an upper direction causing the lower loop to glide over the second thread end until the lower loop is tied to the wound, but leaving the upper loop in a loose state; and
   g) pulling by hand the second thread end causing the upper loop to glide over the first thread end, placing the upper loop in a closed position adjacent to the wound and closed lower loop.

* * * * *